(12) United States Patent
Mattingly et al.

(10) Patent No.: US 8,357,495 B2
(45) Date of Patent: *Jan. 22, 2013

(54) IMMUNOASSAY OF ANALYTES IN SAMPLES CONTAINING ENDOGENOUS ANTI-ANALYTE ANTIBODIES

(75) Inventors: Phillip G. Mattingly, Third Lake, IL (US); Maciej Adamczyk, Gurnee, IL (US); Roy Jeffrey Brashear, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/429,592

(22) Filed: Apr. 24, 2009

(65) Prior Publication Data

US 2009/0246800 A1    Oct. 1, 2009

Related U.S. Application Data

(63) Continuation-in-part of application No. PCT/US2007/081608, filed on Oct. 17, 2007.

(60) Provisional application No. 60/854,569, filed on Oct. 26, 2006.

(51) Int. Cl.
*G01N 33/53* (2006.01)

(52) U.S. Cl. .................................. 435/7.1; 436/518

(58) Field of Classification Search .................. None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,637,880 A | 1/1987 | Halbert |
| 4,956,778 A | 9/1990 | Naito |
| 5,006,309 A | 4/1991 | Khalil et al. |
| 5,063,081 A | 11/1991 | Cozzette et al. |
| 5,089,424 A | 2/1992 | Khalil et al. |
| 5,091,513 A | 2/1992 | Huston et al. |
| 5,132,405 A | 7/1992 | Huston et al. |
| 5,244,630 A | 9/1993 | Khalil et al. |
| 5,534,615 A | 7/1996 | Baker et al. |
| 5,561,049 A | 10/1996 | Vold et al. |
| 5,741,654 A | 4/1998 | Michel et al. |
| 5,795,725 A | 8/1998 | Buechler et al. |
| 5,981,180 A | 11/1999 | Chandler et al. |
| 6,174,686 B1 | 1/2001 | Buechler et al. |
| 6,309,888 B1 | 10/2001 | Holvoet et al. |
| 6,537,760 B1 | 3/2003 | Bergmann et al. |
| 6,670,115 B1 | 12/2003 | Zhang |
| 6,682,648 B1 | 1/2004 | MacPhee et al. |
| 6,887,714 B2 | 5/2005 | Fritsch et al. |
| 6,896,872 B2 | 5/2005 | Dambinova |
| 7,045,310 B2 | 5/2006 | Buck, Jr. et al. |
| 7,045,364 B2 | 5/2006 | Limoges et al. |
| 7,064,189 B2 | 6/2006 | Salcedo et al. |
| 7,196,169 B2 | 3/2007 | Van Eyk et al. |
| 7,258,994 B2 | 8/2007 | Vojdani |
| 7,285,418 B2 | 10/2007 | Katrukha et al. |
| 7,348,157 B2 | 3/2008 | Eriksson et al. |
| 7,407,767 B2 | 8/2008 | Honjo et al. |
| 7,776,605 B2 | 8/2010 | Mattingly et al. |
| 2003/0100036 A1 | 5/2003 | Vojdani |
| 2003/0170881 A1 | 9/2003 | Davis et al. |
| 2004/0018577 A1 | 1/2004 | Emerson Campbell |
| 2004/0091934 A1 | 5/2004 | Narvanen et al. |
| 2004/0219538 A1 | 11/2004 | Chou et al. |
| 2004/0219604 A1 | 11/2004 | Eriksson et al. |
| 2005/0054078 A1 | 3/2005 | Miller et al. |
| 2005/0181451 A1 | 8/2005 | Bates |
| 2006/0024744 A1 | 2/2006 | Mills et al. |
| 2006/0024749 A1 | 2/2006 | Dambinova |
| 2006/0040288 A1 | 2/2006 | Richardson et al. |
| 2006/0094056 A1 | 5/2006 | Chappell et al. |
| 2006/0160164 A1 | 7/2006 | Miller et al. |
| 2006/0246525 A1 | 11/2006 | Honjo et al. |
| 2007/0012888 A1 | 1/2007 | Bichay |

(Continued)

FOREIGN PATENT DOCUMENTS

EP            273115 A2      7/1988

(Continued)

OTHER PUBLICATIONS

Janeway et al. (Immunobiology 1997 third edition, three pages, including p. 2:9, 2:10 and 2:32).*
Adamczyk M., et al., "Circulating Cardiac Troponin-I Autoantibodies in Human Plasma and Serum," Annals of the New York Academy of Sciences, 2009, vol. 1173, pp. 67-74.
Akerstrom B., et al., "Protein G: A Powerful Tool for Binding and Detection of Monoclonal and Polyclonal Antibodies," Immunology, 1985, vol. 135 (4), pp. 2589-2592.
Asai D.J., "Antibodies in Cell Biology" in: Methods in Cell Biology, vol. 37, Academic Press Inc., 1993, Table of Contents.
Barnes D., et al., "Serum-Free Cell Culture: A Unifying Approach," Cell, 1980, vol. 22 (3), pp. 649-655.

(Continued)

*Primary Examiner* — Jacob Cheu
(74) *Attorney, Agent, or Firm* — Audrey L. Bartnicki; Emily Haliday, Weaver, Austin, Villeneuve & Sampson LLP (57) ABSTRACT

The disclosure provides among other things an assay method that compensates for the presence of endogenous antibodies, e.g., autoantibodies, which might otherwise compromise the measurement of an analyte in a biological sample. In one embodiment, this method entails the use of a two labeled entities: a labeled detection agent and a labeled species-specific antibody, wherein the labeled species-specific antibody is specific for the species from which the biological sample was obtained. Sample analyte is bound by the detection agent and any anti-analyte autoantibodies present in the sample. Analyte bound by autoantibodies is detected via the species-specific antibody, optionally labeled.

26 Claims, 4 Drawing Sheets

U.S. PATENT DOCUMENTS

| | | | |
|---|---|---|---|
| 2007/0037227 A1 | 2/2007 | Hanash et al. | |
| 2007/0172888 A1 | 7/2007 | Hallermayer et al. | |
| 2008/0305512 A1* | 12/2008 | Mattingly et al. | 435/28 |
| 2009/0017560 A1 | 1/2009 | Adamczyk et al. | |
| 2010/0311079 A1 | 12/2010 | Mattingly et al. | |
| 2011/0136103 A1 | 6/2011 | Adamczyk et al. | |

FOREIGN PATENT DOCUMENTS

| | | | |
|---|---|---|---|
| EP | 326100 A2 | 8/1989 |
| EP | 406473 A1 | 1/1991 |
| EP | 0424634 A2 | 5/1991 |
| EP | 0425633 A1 | 5/1991 |
| EP | 425633 B1 | 7/1994 |
| EP | 273115 B1 | 9/1994 |
| EP | 424634 B1 | 6/1995 |
| EP | 406473 B1 | 9/1995 |
| EP | 326100 B1 | 9/1996 |
| EP | 1271152 A1 | 1/2003 |
| EP | 1473567 A1 | 11/2004 |
| EP | 1619498 A2 | 1/2006 |
| EP | 1473567 B1 | 7/2006 |
| EP | 1149914 B1 | 6/2008 |
| EP | 2097749 A2 | 9/2009 |
| EP | 2097750 A2 | 9/2009 |
| EP | 2115466 A2 | 11/2009 |
| WO | WO9963345 A1 | 12/1999 |
| WO | WO03016575 A1 | 2/2003 |
| WO | WO2004091476 A2 | 10/2004 |
| WO | WO2006043891 A1 | 4/2006 |
| WO | WO2007085411 A1 | 8/2007 |
| WO | WO2008051761 A2 | 5/2008 |
| WO | WO2008051762 A2 | 5/2008 |
| WO | WO2008080030 A2 | 7/2008 |

OTHER PUBLICATIONS

Bohner J., et al., "False-Negative Immunoassay Results for Cardiac Troponin I Probably Due to Circulating Troponin I Autoantibodies," Clinical Chemistry, 1996, vol. 42 (12), pp. 2046.

Bui M.N., et al., "Autoantibody Titers to Oxidized Low-Density Lipoprotein in Patients with Coronary Atherosclerosis," American Heart Journal, 1996, vol. 131 (4), pp. 663-667.

Butler, et al."Mammalian Cell Biotechnology—A Practical Apporach",1991,272,1-8.

Caforio A.L., et al., "Circulating Cardiac Autoantibodies in dilated Cardiomyopathy and Myocarditis: pathogenetic and Clinical significance," The European Journal of Heart Failure, 2002, vol. 4 (4), pp. 411-417.

Caforio A.L., et al., "Autoimmunity in Myocarditis and Dilated Cardiomyopathy: Cardiac Autoantibody Frequency and Clinical Correlates in a Patient Series from Italy," Giornale Italiano Di Cardiologia, 1997, vol. 27 (2), pp. 106-112.

Caforio, et al., "Autoimmune Myocarditis and Dilated Cardiomyopathy: Focus on Cardiac Auto Antibodies," Lupus, 2005, vol. 14 (9), pp. 652-655.

Clackson T., et al., "Making Antibody Fragments Using Phage Display Libraries," Nature, 1991, vol. 352, pp. 624-628.

Cohen S.N., et al., "Non Chromosomal Antibiotic Resistance in Bacteria: Genetic Transformationof Escherichia coli by R-Factor Dna," Proceedings of the National Academy of Sciences, 1972, vol. 69 (8), pp. 2110-2114.

Coligan J.E., et al., "Peptides" in: Current Protocols in Immunology, John Wiley & Sons, 1991.

Dennis M.S., et al., "Binding Interactions of Kistrin Withplatelet Glycoprotein Iib-Iiia: Analysis Bysite-Directed Mutagenesis," Proteins, 1993, vol. 15 (3), pp. 312-321.

Dighiero G., et al., "Sera with High Levels of Anti-Smooth Muscle and Anti-Mitochondrial Antibodies Frequently Bind to Cytoskeleton Proteins," Clinical and Experimental Immunology, 1990, vol. 82 (1), pp. 52-56.

Eriksson S., et al., "An Interfering Component in Cardiac Troponin I Immunoassays—Its Nature and Inhibiting Effect on the Binding of Antibodies against Different Epitopes," Clinical Biochemistry, 2004, vol. 37 (6), pp. 472-480.

Eriksson S., et al., "Autoantibodies against Cardiac Troponins," New England Journal of Medicine, 2005, vol. 352 (1), pp. 98-100.

Eriksson S., et al., "Beliefs in Cardiac Troponin Testing," Clinical Chemistry, 2005, vol. 51 (9), pp. 1755-1756.

Eriksson S., et al., "Comparison of Cardiac Troponin I Immunoassays Variably Affected by Circulating Autoantibodies," Clinical Chemistry, 2005, vol. 51 (5), pp. 848-855.

Eriksson S., et al., "Negative Interference in Cardiac Troponin I Immunoassays by Circulating Troponin Autoantibodies," Clinical Chemistry, 2005, vol. 51 (5), pp. 839-847.

Eriksson S., et al., "Negative Interference in Cardiac Troponin I Immunoassays from a Frequently Occurring Serum and Plasma Component," Clinical Chemistry, 2003, vol. 49 (7), pp. 1095-1104.

Eriksson S., et al., "The Interfering Component in Cardiac Troponin I Immunoassays," Clinical Chemistry, 2004, vol. 50 (6), pp. 1101-1102.

Filippantos G., et al., "An Introduction to Acute Heart Failure Syndromes: Definition and Classification," Heart Failure Reviews, 2007, vol. 12 (2), pp. 87-90.

Frostegard J.,, "Atherosclerosis in Patients with Autoimmune Disorders," Arteriosclerosis, Thrombosis, and Vascular Biology, 2005, vol. 25, pp. 1776-1785.

Gorman C.M., et al., "Transient Production of Proteins Using an Adenovirus Transformed Cell Line", DNA and Prot. Eng. Tech., 1990, 2 (1), 3-10.

Goser S., et al., "Cardiac Troponin I But not Cardiac Troponin T Induces Severe Autoimmune Inflammation in the Myocardium," Circulation, 2006, vol. 114 (16), pp. 1693-1702.

Griffiths A.D., et al., "Human Anti-Self Antibodies with High Specificity from Phage Display Libraries," European Molecular Biology Organization, 1993, vol. 12 (2), pp. 725-734.

Gurlek A., et al., "Association Between Anticardiolipin Antibodies and Recurrent Cardiac Events in Patients with Acute Coronary Syndrome," International Heart Journal, 2005, vol. 46 (4), pp. 631-638.

Haralambous S., et al., "Increased Natural Autoantibody Activity to Cytoskeleton Proteins in Sera from Patients with Necrobiosis Lipoidica, with or without Insulin-Dependent Diabetes Mellitus," Autoimmunity, 1995, vol. 20 (4), pp. 267-275.

Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.

Huston J.S., et al., "Protein Engineering of Antibody Binding Sites: Recovery of Specific Activity in an Anti-Digoxin Single-Chain Fv Analogue Produced in Escherichia coli," Proceedings of the National Academy of Sciences of the USA, 1988, vol. 85 (16), pp. 5879-5883.

International Preliminary Report on Patentability and Written Opinion for Application No. PCT/US07/081608, mailed on Apr. 28, 2009, 8 pages.

International Preliminary Report on Patentability and Written Opinion for Application No. PCT/US07/088477, mailed on Jun. 24, 2009, 4 pages.

International Preliminary Report on Patentability and Written Opinion for Application No. PCT/US2007/081606, mailed on Apr. 28, 2009, 4 pages.

International Search Report and Written Opinion for Application No. PCT/US07/88477, mailed on Aug. 5, 2008, 9 pages.

International Search Report and Written Opinion for Application No. PCT/US2007/081606, mailed on Sep. 9, 2008, 6 pages.

International Search Report and Written Opinion for Application No. PCT/US2007/081608, mailed on May 27, 2008, 14 pages.

International Search Report for Application No. PCT/US2007/018608, mailed on May 27, 2008, 14 pages.

ISA/EP Extended European Search Report for Application No. EP07871173 dated Nov. 18, 2009, 9 pages.

Jahns R., et al., "$\beta_1$-Adrenergic Receptor Function, Autoimmunity, and Pathogenesis of Dilated Cardiomyopathy," Trends in Cardiovascular Medicine, 2006, vol. 16 (1), pp. 20-24.

Kenny P.R., et al., "Falsely Elevated Cardiac Troponin-I in Patients with Seropositive Rheumatoid Arthritis," Journal of Rheumatology, 2005, vol. 32 (7), pp. 1258-1261.

Koga K., et al., "Western-Blotting Method for Detecting Antibodies against Human Muscle Contractile Proteins in Myositis," Journal of Immunology Methods, 1987, vol. 105 (1), pp. 15-21.

Kohler G., et al., "Continuous Cultures of Fused Cells Secreting Antibody of Predefined Specificity," Nature, 1975, vol. 256 (5517), pp. 495-497.

Kronvall G., "A Surface Component in Group A, C, and G Streptococci with Non-Immune Reactivity for Immunoglobulin G," Journal of Immunology, 1973, vol. 111 (5), pp. 1401-1406.

Leuschner F., et al., "Absence of Auto-Antibodies against Cardiac Troponin I Predicts Improvement of Left Ventricular Function after Acute Myocardial Infarction," European Heart Journal, 2008, vol. 29 (16), pp. 1949-1955.

Liao Y.H., et al., "Autoantibodies against the $\alpha_1$-Adrenoceptor Related with the Increased Stroke Recurrence in Hypertensive Patients," Circulation, 2005, 112 (17), pp. 346.

Luther P., et al. , "$\alpha_1$-Adrenergic Receptor Antibodies in Patients With Primary Hypertension," Hypertension, 1997, vol. 29, pp. 678-682.

Maisch B., et al., "Inflammatory Dilated Cardiomyopathy (DCMI)," Herz, 2005, vol. 30 (6), pp. 535-544.

Marks J.D., et al., "By-passing Immunization. Human Antibodies from V-gene Libraries Displayed on Phage," Journal of Molecular Biology, 1991, vol. 222 (3), pp. 581-597.

Marks J.D., et al., "By-Passing Immunization: Building High Affinity Human Antibodies by Chain Shuffling," Biotechnology, 1992, vol. 10 (7), pp. 779-783.

Mather Jennie P., "Mammalian Cell Culture ", The Use of Serum-Free Hormone-Supplemented Media,1984,1-9.

Matsui S., et al., "Dilated Cardiomyopathy Defines Serum Cardiovascular Receptors Auto Antibodies Against G-Protein-Coupled Cardiovascular Receptors," Autoimmunity, 1995, vol. 21 (2), pp. 85-88.

McCafferty J., et al., "Phage Antibodies: Filamentous Phage Displaying Antibody Variable Domains," Nature, 1990, vol. 348, pp. 552-554.

Merrifield R.B., et al., "Solid Phase Peptide Synthesis. I. The Synthesis of a Tetrapeptide," Journal of the American Chemical Society, 1963, vol. 85, pp. 2149-2154.

Michels V.V., et al, "Circulating Heart Autoantibodies in Familial as Compared With Nonfamilial Idiopathic Dilated Cardiomyopathy," Mayo Clin. Proc., 1994, vol. 69(1), pp. 24-27.

Okazaki T., et al., "Autoantibodies against Cardiac Troponin I are Responsible for Dilated Cardiomyopathy in PD-1-Deficient Mice," Nature Medicine, 2003, vol. 9 (12), pp. 1477-1483.

Okazaki T., et al., "Pathogenic Roles of Cardiac Autoantibodies in Dilated Cardiomyopathy," Trends in Molecular Medicine , 2005, vol. 11 (7), pp. 322-326.

Panteghini M., "Selection of Antibodies and Epitopes for Cardiac Troponin Immunoassays: Should we Revise our Evidence-Based Beliefs?," Clinical Chemistry, 2005, vol. 51 (5), pp. 803-804.

Quintana F.J., et al., "Antigen microarrays identify unique serum autoantibody signatures in clinical and pathologic subtypes of multiple sclerosis," Proceedings of the National Academy of Sciences, 2008, vol. 105 (48), pp. 18889-18894.

Sherer Y., et al., "Coronary Artery Disease but not Coronary Calcification is Associated with Elevated Levels of Cardiolipin, Beta-2-Glycoprotein-I, and Oxidized LDL Antibodies," Cardiology, 2001, vol. 95 (1), pp. 20-24.

Shmilovich H., et al., "Autoantibodies to Cardiac Troponin I in Patients with Idiopathic Dilated and Ischemic Cardiomyopathy," International Journal of Cardiology, 2007, vol. 117 (2), pp. 198-203.

Stewart J.M., et al., Solid-Phase Peptide Synthesis, 2nd Edition, Pierce Chemical Company, 1984, Table of Contents.

Stites D.P., et al., eds., "Basic and Clinical Immunology", 7th Edition, Appleton & Lange, 1991, Table of Contents.

Supplementary European Search Report for Application No. EP07869697, mailed on Jun. 24, 2010, 9 pages.

Takaya M., et al., "Antibodies against Myofibrillar Proteins in Myasthenia Gravis Patients" Tokai Journal of Experimental and Clinical Medicine, 1992, vol. 17 (1), pp. 35-39.

Takeda N., et al., "Cardiomyopathy: Molecular and Immunological Aspects (Review)," International Journal of Molecular Medicine, 2003, vol. 11 (1), pp. 13-16.

Vaitukaitis J.L., "Production of Antisera with Small Doses of Immunogen: Multiple Intradermal Injections," Methods in Enzymology, 1981, vol. 73 (Pt B), pp. 46-52.

Wu A.H., "Cardiac Troponin: Friend of the Cardiac Physician, Foe to the Cardiac Patient?" Circulation, 2006, vol. 114 (16), pp. 1673-1675.

Zammanou A., et al., "Anti-Smooth Muscle Antibodies (ASMAs) and Anti-Cytoskeleton Antibodies (ACTAs) in Liver Diseases: A Comparison of Classical Indirect Immunofluorescence with ELISA," Journal of Clinical Laboratory Analysis, 2002, vol. 16, pp. 194-201.

Zhang Lin, et al., "Study of autoantibodies against G-protein-coupled $\beta_2$- and $\alpha_1$-adrenergic and angiotensin II type 1 receptors in patients with dilated cardiomyopathy", Journal of Oncology, 2002, vol. 30 (6), pp. 363-365.

Zhang Lin, et al., "Study of autoantibodies against G-protein-coupled $\beta_2$2- and $\alpha_1$-adrenergic and angiotensin II-1 receptors in patients with chronic heart failure", Journal of oncology, 2003, 31 (1), 17-20.

Zhong M., et al, "Distribution and Biological Effects of Autoantibody Against $\alpha_1$-Adrenoceptor in Patients with Primary Hypertension," Circulation, 2006, 114 (18), pp. 494.

\* cited by examiner

Symbol key:

Detection antibody

Analyte

Capture antibody

Solid support

Auto-antibody

Anti-human detection antibody

Standard immunoassay (no autoantibody):

IMMUNOASSAY OF ANALYTES IN SAMPLES CONTAINING ENDOGENOUS ANTI-ANALYTE ANTIBODIES

CROSS REFERENCE TO RELATED APPLICATIONS

This application is a continuation-in-part application of PCT International Application PCT/US2007/081608 filed Oct. 17, 2007 (expired), and claims the priority of U.S. Provisional Application Ser. No. 60/854,569 filed Oct. 26, 2006 (expired), the disclosures of which are incorporated herein by reference in their entireties.

TECHNICAL FIELD

The present disclosure relates generally to the area of immunoassay of analytes in samples that may contain antibodies (e.g., interfering autoantibodies) reactive with the target analyte. In particular, the disclosure relates among other things to methods and compositions that facilitate assaying for analytes in the presence of autoantibodies, and kits and kit components that can be employed for same.

BACKGROUND

Many patients have circulating antibodies to analytes of clinical interest. Conventional sandwich immunoassays, which include two or more analyte-specific antibodies, are subject to interference from analyte-reactive endogenous antibodies (e.g., autoantibodies). For example, when the assay antibodies and the endogenous antibodies bind to the same or overlapping regions of the analyte, the endogenous antibodies will compete for binding with the endogenous antibodies, leading to erroneously low results. This interference by endogenous antibodies can produce false negative results, such that individuals at risk for, or suffering from, a particular disease fail to be diagnosed.

In view of the importance of accurate detection of analytes of clinical interest, there clearly remains a need for assays, methods, and kits, and components thereof which avoid, minimize or overcome interference by endogenous antibodies.

This background information is provided for the purpose of making known information believed by the applicant to be of possible relevance to the present disclosure. No admission is necessarily intended, nor should be construed, that any of the preceding information constitutes prior art against the present disclosure.

SUMMARY

The disclosure provides among other things methods, assays compositions, kits, and kit components to facilitate assaying for analytes in the presence of endogenous anti-analyte antibodies (e.g., autoantibodies).

The disclosure provides as an embodiment an immunoassay method that entails contacting a biological sample being tested for an analyte of interest with: (i) a detection agent (e.g., an antibody) that binds the analyte under conditions sufficient for binding of the detection agent to any analyte of interest present in the sample so as to form a detection agent/analyte complex; and (ii) a species-specific antibody, wherein the species-specific antibody is specific for the species from which the biological sample was obtained and specifically binds endogenous anti-analyte antibody, under conditions sufficient for specific binding of the species-specific antibody to any endogenous anti-analyte antibody present in the sample and bound and bound to the detection agent/analyte complex so as to form a species-specific antibody/endogenous anti-analyte antibody/analyte/detection agent complex. Detection is done of the one or more complex(es) including the detection agent bound to analyte (detection agent/analyte complex) and/or the species-specific antibody bound to endogenous anti-analyte antibody (species-specific antibody/anti-analyte antibody complex), wherein the amount of the one or more complex(es) is positively correlated with the concentration of analyte present in the sample. In certain embodiments, the endogenous anti-analyte antibody is an anti-analyte autoantibody.

Moreover, optionally the assay can be done where the detection agent and the species-specific antibody are labeled, either prior to or sometime during the assay. With such labeling, optionally the detection step comprises detecting a signal from the label of one or more complex(es) comprising the detection agent/analyte and/or the species-specific antibody/anti-analyte antibody, wherein the signal is positively correlated with the concentration of analyte present in the sample.

In particular embodiments, the method additionally includes contacting the biological sample with a capture agent affixed to a solid phase where the capture agent binds analyte, and detection entails detecting a signal from species-specific antibody bound to endogenous anti-analyte antibody, which are affixed to the solid phase.

In certain embodiments where the detection agent and the species-specific antibody are labeled. The labeled detection agent and the labeled species-specific antibody are labeled with either the same label or with different labels.

The biological sample can be contacted with the detection agent and the species-specific antibody simultaneously or sequentially. If a capture agent is employed, the capture agent optionally binds to a different site on the analyte than does the detection agent. The detection agent and/or the species-specific antibody can be contacted with the biological sample simultaneously with the contacting of the biological sample with the capture agent. Alternatively, the contacting of the detection agent and/or the species-specific antibody with the biological sample can be carried out sequentially with the contacting of the biological sample with the capture agent, in any order.

In an exemplary embodiment, the immunoassay method entails contacting a biological sample with a capture agent affixed to a solid phase where the capture agent bind analyte, under conditions sufficient for binding of the capture agent to analyte to form a solid phase-affixed complex. The biological sample is also contacted with: (i) a detection agent that binds the analyte under conditions sufficient for binding of the detection agent to any analyte present in the capture agent/analyte complex so as to form a solid phase-affixed detection agent/analyte/capture agent complex; and (ii) a species-specific antibody, wherein the species-specific antibody is specific for the species from which the biological sample was obtained and specifically binds endogenous anti-analyte antibody, under conditions sufficient for specific binding of the species-specific antibody to any anti-analyte autoantibody bound to the capture agent/analyte complex so as to form a solid phase-affixed species-specific antibody/anti-analyte autoantibody/analyte/capture agent complex. The one or more solid phase-affixed complex(es) (e.g., the solid phase-affixed detection agent/analyte/capture agent complex and the solid phase-affixed species-specific antibody/anti-analyte autoantibody/analyte/capture agent complex) are detected, and the amount of these complexes is positively correlated with the concentration of analyte present in the sample.

Optionally the assay can be done where the detection agent and the species-specific antibody are labeled, either prior to or sometime during the assay. With such labeling, optionally the detection step comprises detecting a signal from the label of one or more solid-phase affixed complex(es), wherein the signal is positively correlated with the concentration of analyte present in the sample.

In another exemplary embodiment, the immunoassay method entails contacting a biological sample with one or more anti-analyte capture antibodies affixed to a solid phase where the capture antibody specifically binds analyte, under conditions sufficient for specific binding of the capture antibody to analyte to form a solid phase-affixed capture antibody/analyte complex (e.g., a solid phase-affixed immune complex). The biological sample is also contacted with: (i) one or more anti-analyte antibodies that bind analyte under conditions sufficient for binding of the one or more anti-analyte antibodies to any analyte present in the capture agent/analyte complex so as to form one or more solid phase-affixed anti-analyte antibody/analyte/capture antibody complexes; and (ii) a species-specific antibody, wherein the species-specific antibody is specific for the species from which the biological sample was obtained and specifically binds endogenous anti-analyte antibody, under conditions sufficient for specific binding of the species-specific antibody to any anti-analyte autoantibody present in the sample and bound to the capture antibody/analyte complex so as to form a solid phase-affixed species-specific antibody/anti-analyte autoantibody/analyte/capture antibody complex. the one or more solid phase-affixed complex(es) (e.g., solid phase-affixed anti-analyte antibody/analyte/capture antibody complex and solid phase-affixed species-specific antibody/anti-analyte autoantibody/analyte/capture antibody complex) are detected and the amount of these complexes is positively correlated with the concentration of analyte present in the sample.

In certain embodiments, the anti-analyte antibody and the species-specific antibody are labeled, optionally with the either same label or with different labels. With such labeling, the detection step optionally comprises detecting a signal from the label of the one or more solid-phase affixed complex(es), wherein the signal is positively correlated with the concentration of analyte present in the sample.

The anti-analyte capture antibody and labeled anti-analyte antibody and/or the species-specific antibody can be contacted with the biological sample simultaneously or sequentially, in any order. In particular embodiments, the anti-analyte antibody and the species-specific antibody are contacted with the biological sample simultaneously. In other embodiments, the anti-analyte antibody and the species-specific antibody are contacted with the biological sample sequentially, in any order.

In particular embodiments of the methods of the disclosure, the biological sample is obtained from subject that is a mammal (e.g., optionally human).

The disclosure also provides test kits. In certain embodiments, the test kit includes a detection agent specific for an analyte and a species-specific antibody, wherein the species-specific antibody is specific for the species from which the biological sample is to be obtained and specifically binds endogenous anti-analyte antibody. In exemplary embodiments, the species-specific antibody is a human-specific antibody.

If desired, the test kit can also include a solid phase and a capture agent, such as an anti-analyte capture antibody, affixed to the solid phase. Alternatively, or in addition, the detection agent and the species-specific antibody can be labeled. The labeled detection agent and the labeled species-specific antibody can be labeled with the same label or with different labels. In exemplary embodiments, the labeled detection agent is a labeled anti-analyte antibody. In such embodiments, the labeled anti-analyte antibody and the labeled species-specific antibody can be present in the same container or in different containers.

Any label employed in the disclosure can be a direct label (such as an acridinium-9-carboxamide) or an indirect label. In certain embodiments of the disclosure, at least one label is contacted with an indicator reagent to produce a detectable signal.

Any solid phase employed in the disclosure can include a microparticle. Suitable microparticles can be magnetic or paramagnetic. Microplates and/or electrodes can also be employed as a solid phase.

In particular embodiments, useful for multiplex formats, the solid phase employed in a method or test kit of the disclosure can include a plurality of anti-analyte capture antibodies that are specific for a plurality of different analytes. In variations of these embodiments, the biological sample can be contacted with a plurality of different labeled anti-analyte antibodies that are specific for said plurality of different analytes, wherein each different labeled anti-analyte antibody is labeled with a distinct label. Such antibodies can be included in test kits according to the disclosure. In an exemplary multiplex format, the solid phase employed in a method or test kit of the disclosure includes a plurality of electrodes, each electrode bearing a different anti-analyte capture antibody.

BRIEF DESCRIPTION OF THE DRAWINGS

FIGS. 1A-B illustrate a sandwich immunoassay.

FIG. 2 illustrates an exemplary embodiment of the claimed invention intended for use in assaying human samples. Symbols are as depicted in FIG. 1(A). As shown in this figure the inclusion in the assay of a labeled anti-human (species-specific) antibody counters the diminution in signal attributable to the presence of interfering endogenous antibodies (e.g., autoantibodies). Essentially, a binding site formerly usurped by an interfering endogenous antibody (e.g., autoantibody) has been rendered accessible and accounted for in the assay by virtue of inclusion of a labeled anti-human (species specific) detection agent such as a detection antibody.

DETAILED DESCRIPTION

Embodiments of the disclosure include an assay method that optionally compensates for the presence of endogenous antibodies (e.g., autoantibodies), which might otherwise compromise the measurement of an analyte of interest in a biological sample. This method generally entails the use of a two components: a detection agent and a species-specific antibody, wherein the species-specific antibody is specific for the species from which the biological sample was obtained.

Sample analyte is bound by the detection agent and any endogenous anti-analyte antibodies present in the sample. Analyte bound by endogenous antibodies is detected via the species-specific antibody.

DEFINITIONS

Unless specifically defined otherwise as follows, all technical, scientific, and other terms used herein have the same meaning as commonly understood by one of ordinary skill in the art to which this invention belongs.

"Biological samples" that can be assayed using the methods of the present disclosure include biological fluids, such as whole blood, serum, plasma, synovial fluid, cerebrospinal fluid, bronchial lavage, ascites fluid, bone marrow aspirate, pleural effusion, urine, as well as tumor tissue or any other bodily constituent or any tissue culture supernatant that could contain the analyte of interest.

"Analyte," or "analyte of interest" as used herein, refers to the substance to be detected, which may be present in the biological sample. The analyte can be any substance for which there exists a naturally occurring specific binding partner or for which a specific binding partner can be prepared. Thus, an analyte is a substance that can bind to one or more specific binding partners in an assay. The analyte can include a protein, a peptide, an amino acid, a hormone, a steroid, a vitamin, a drug, including those administered for therapeutic purposes as well as those administered for illicit purposes, a bacterium, a virus, and metabolites of or antibodies to any of the above substances. As a member of a specific binding pair, the analyte can be detected by means of naturally occurring specific binding partners, such as the use of intrinsic factor protein as capture and/or detection agents for the determination of vitamin B12 or the use of a lectin as capture and/or detection agents for the determination of a carbohydrate.

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Furthermore, specific binding partners can include partner(s) that is/are analog(s) of the original specific binding partner, for example, an analyte-analog. Immunoreactive specific binding partners include antigens, antigen fragments, antibodies and antibody fragments, both monoclonal and polyclonal, and complexes thereof, including those formed by recombinant DNA methods.

The term "specific binding" is defined herein as the preferential binding of binding partners to another (e.g., two polypeptides, a polypeptide and nucleic acid molecule, or two nucleic acid molecules) at specific sites, as determined by means known in the art. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

A "solid phase," as used herein, refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

As used herein, term "microparticle" refers to a small particle that is recoverable by ultracentrifugation. Microparticles typically have an average diameter on the order of about 1 micron or less.

The term "capture agent" is used herein to refer to a binding partner that binds to analyte, preferably specifically. Capture agents can be attached to a solid phase. As used herein, the binding of a solid phase-affixed capture agent to analyte forms a "solid phase-affixed complex."

The term "labeled detection agent" is used herein to refer to a binding partner that binds to analyte, preferably specifically, and is labeled with a detectable label or becomes labeled with a detectable label during use in an assay.

A "detectable label" includes a moiety that is detectable or that can be rendered detectable.

As used with reference to a labeled detection agent, a "direct label" is a detectable label that is attached, by any means, to the detection agent.

As used with reference to a labeled detection agent, an "indirect label" is a detectable label that specifically binds the detection agent. Thus, an indirect label includes a moiety that is the specific binding partner of a moiety of the detection agent. Biotin and avidin are examples of such moieties that are employed, for example, by contacting a biotinylated antibody with labeled avidin to produce an indirectly labeled antibody.

As used herein, the term "indicator reagent" refers to any agent that is contacted with a label to produce a detectable signal. Thus, for example, in conventional enzyme labeling, an antibody labeled with an enzyme can be contacted with a substrate (the indicator reagent) to produce a detectable signal, such as a colored reaction product.

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

As used herein, a "species-specific antibody" refers to an antibody that specifically binds target antibodies from a particular species, regardless of the antigen-binding specificity of the target antibodies.

A "human-specific antibody" is an antibody that specifically binds human antibodies, e.g., human autoantibodies.

As used herein, an "anti-analyte antibody" refers to an antibody that binds analyte. In certain embodiments, the anti-analyte antibody binds analyte specifically.

An "anti-analyte capture antibody" is an anti-analyte antibody that captures analyte. Such antibodies are conveniently affixed to a solid phase, and, if so, the binding of an antibody to analyte forms a "solid phase-affixed immune complex."

A "labeled anti-analyte antibody" is an anti-analyte antibody that is labeled with a detectable label or that becomes labeled with a detectable label during immunoassay.

An "endogenous anti-analyte antibody" is an antibody that is naturally occurring in an individual (i.e., the individual from which the biological sample being analyzed is taken) and that binds to an analyte of interest.

An "anti-analyte autoantibody" is an antibody that specifically binds to an analyte that is naturally occurring in the individual in which the antibody is produced. This antibody is, or becomes, labeled with a detectable label.

Immunoassay Methods
In General

The immunoassay methods of the disclosure can be carried out in any of a wide variety of formats. For a general review of immunoassays, see Methods in Cell Biology Volume 37: Antibodies in Cell Biology, Asai, ed. Academic Press, Inc. N.Y. (1993); Basic and Clinical Immunology 7th Edition, Stites & Terr, eds. (1991), which is incorporated by reference in its entirety.

In particular embodiments, the method entails contacting a biological sample with a detection agent under conditions sufficient for binding of the detection agent to any analyte present in the sample. The biological sample is also contacted with a species-specific antibody, wherein the species-specific antibody is specific for the species from which the biological sample was obtained, under conditions sufficient for specific binding of the species-specific antibody to any endogenous anti-analyte antibody present. The sample may be contacted with the detection agent and the species-specific antibody simultaneously or sequentially, in any order.

A signal is then detected from complex(es) including the detection agent bound to any analyte present in the sample and/or the species-specific antibody bound to any endogenous anti-analyte antibody present in the sample. The signal is positively correlated with the concentration of analyte present in the sample. In exemplary embodiments, the endogenous anti-analyte antibody detected is an anti-analyte autoantibody.

In certain embodiments, the method also entails contacting the biological sample with a capture agent affixed to a solid phase, under conditions sufficient for binding of the capture agent to analyte to form a solid phase-affixed complex. In such embodiments, the signal is detected from the solid phase-affixed complex(es). In preferred embodiments, the capture agent is an antibody (i.e., a capture antibody).

In specific embodiments, the detection agent and the species-specific antibody are labeled. Such embodiment may, but need not, also employ a capture agent affixed to a solid phase.

In exemplary embodiments, the method is carried out in a "sandwich immunoassay" format. In particular, the biological sample is contacted with a capture agent affixed to a solid phase, under conditions sufficient for binding of the capture agent to analyte to form a solid phase-affixed complex. In such embodiments, the signal is detected from the solid phase-affixed complex(es). In preferred embodiments, the capture agent is an antibody (i.e., a capture antibody).

The biological sample is also contacted with the labeled detection agent under conditions sufficient for binding of the labeled detection agent to analyte. In preferred embodiments, the labeled detection agent is an antibody (i.e., a detection antibody). Furthermore, the biological sample is contacted with the labeled species-specific antibody, under conditions sufficient for specific binding of the labeled species-specific antibody to any anti-analyte autoantibody present.

In embodiments employing a solid phase, the sample may be contacted with the solid phase, the detection agent, and the species-specific antibody simultaneously or sequentially, in any order. Furthermore, the sample may be contacted with any two of these components simultaneously, followed by contact with the remaining component. Regardless of the order of contact, if analyte is present in the sample, a solid phase-affixed complex forms that contains the analyte "sandwiched" between the capture agent and the detection agent. If endogenous anti-analyte antibodies (e.g., anti-analyte autoantibodies) are also present in the sample, solid phase-affixed complexes can also contain analyte sandwiched between the capture agent and autoantibody, to which species-specific antibody is bound. The bound entities are separated, if necessary, from free detection agent and species-specific antibody, typically by washing, and the signal from the bound entities is detected.

In embodiments employing a labeled detection agent and a labeled species-specific antibody, these components can be labeled with the same label or different labels that are not differentiated during the label detection (e.g., acridinium-9-carboxamide labels of different structures). This format provides a measure of the amount of analyte present in the sample. In other formats, the labeled detection agent and the labeled species-specific antibody are labeled with different labels. In such formats, the signal attributable to the labeled species-specific antibody is positively correlated with the concentration of endogenous anti-analyte antibody (e.g., anti-analyte autoantibody) bound to analyte present in the sample. The combined signal attributable to the two different labels provides a measure of the amount of analyte present in the sample.

Analytes

The immunoassay methods of the disclosure can be employed to detect any analyte for which a capture agent and detection agent can be obtained or produced. The methods of the disclosure are particularly useful for detecting analytes in samples that may contain endogenous antibodies (e.g., autoantibodies) that react with the analyte to be detected. For example, the analyte may be an antigen associated with a pathogen, wherein the antigen is detected in diagnosing and/or monitoring an infectious disease. The presence of endogenous antibodies can interfere with such detection. However, the present disclosure overcomes this problem by allowing the detection of the amount of analyte regardless of binding to endogenous antibody present in the sample.

In an exemplary embodiment, the method is employed to detect an endogenous analyte in a sample that may contain anti-analyte autoantibodies. A large number of endogenous antigens have diagnostic utility in various pathologies, but the presence of autoantibodies can confound the results. The immunoassays of the disclosure can be employed to allow reliable measurements of antigen levels in the presence of such antibodies. Accordingly, the methods of the disclosure are applicable to any endogenous analyte, particularly those having diagnostic or disease assessment utility, and more particularly those assayed in samples that may contain autoantibodies to the endogenous analyte. Examples of such endogenous analytes are shown in Table 1.

TABLE 1

EXEMPLARY ENDOGENOUS ANALYTES $\alpha_1$-adrenoreceptor
$\beta_1$-adrenoreceptor
$\beta_2$-adrenoreceptor
$\alpha$- and $\beta$-myosin heavy chain
Actin
Angiotensin-1 receptor
Annexin V
Brain natriuretic peptide (bNP)
Cardiac troponins
Cardiolipin
Cytoplasmic neutrophils
Endothelial receptor of protein C
Factor VIII
Grehlin
Halogenated protein
Nitrated protein
Heat shock proteins (HSPs; e.g., HSP60, HSP70)
Laminin TABLE 1-continued

EXEMPLARY ENDOGENOUS ANALYTES $M_2$-muscarinic receptor
Myeloperoxidase (MPO)
Oxidized LDL
Placental growth factor
Phospholipids
Prostate-specific antigen (PSA)
Proteinase-3
Prothrombin
Purkinje fibers
Sarcolemmal Na—K-ATPase
Thyroid-stimulating hormone (TSH)
Tissue-type plasminogen activator
Tropomyosin Sample Collection and Processing The immunoassay methods of the disclosure are generally carried out on biological samples derived from an animal, preferably a mammal, and more preferably a human.

As explained above, the methods of the disclosure find particular application in samples that may contain antibodies reactive with the analyte of interest. Thus, the methods of the disclosure are particularly useful, for example, when measuring an endogenous analyte in a sample that may contain anti-analyte autoantibodies. Such antibodies may be present in any of a variety of situations, particularly in pathologies characterized by the release of endogenous proteins from normal or diseased tissue into the blood (e.g., in cardiovascular pathologies or cancer) and especially in autoimmune diseases. Table 2 lists a number of exemplary autoimmune diseases. Samples from individuals at risk for, or diagnosed with, such diseases are amenable to analysis using the methods of the disclosure.

TABLE 2

EXEMPLARY AUTOIMMUNE DISEASES

Insulin-dependent diabetes mellitus (IDDM)
Hashimoto's disease/hypothyroiditis
Graves' disease/hyperthyroiditis
Systemic lupus erythematosus
Sjogren's syndrome
Primary biliary cirrhosis
Mixed connective tissue disease
Chronic active hepatitis
Rheumatoid arthritis
Scleroderma
Myasthenia gravis
Multiple sclerosis
Chronic idiopathic thrombocytopenic purpura
Celiac disease
Inflammatory bowel disease (Crohn's)
Dilated cardiomyopathy (DCM)
Benign prostate hyperplasia (BPH)

The sample may be pretreated as necessary by dilution in an appropriate buffer solution or concentrated, if desired. Any of a number of standard aqueous buffer solutions, employing any of a variety of buffers, such as phosphate, Tris, or the like, at physiological pH, can be used.

Capture Agent

Capture agents useful in the immunoassay methods of the disclosure include those that bind the analyte of interest, preferably specifically, and can be affixed to a solid phase. If the analyte is a ligand, for example, a receptor for the ligand can be employed as the capture agent, and vice versa. However, one or more antibodies are typically most conveniently employed as capture agents.

Solid Phase

For embodiments of the disclosure that employ a solid phase as a support for the capture agent, the solid phase can be any suitable material with sufficient surface affinity to bind a capture agent. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like.

Nitrocellulose has excellent absorption and adsorption qualities for a wide variety of reagents including monoclonal antibodies. Nylon also possesses similar characteristics and also is suitable.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the disclosure can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field.

Microparticles can be suspended in the mixture of soluble reagents and biological sample or can be retained and immobilized by a support material. In the latter case, the microparticles on or in the support material are not capable of substantial movement to positions elsewhere within the support material. Alternatively, the microparticles can be separated from suspension in the mixture of soluble reagents and biological sample by sedimentation or centrifugation. When the microparticles are magnetic or paramagnetic the microparticles can be separated from suspension in the mixture of soluble reagents and biological sample by a magnetic field.

The methods of the present disclosure can be adapted for use in systems that utilize microparticle technology including automated and semi-automated systems wherein the solid phase comprises a microparticle. Such systems include those described in pending U.S. application No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture agent can be attached to the solid phase by adsorption, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase. Ion capture procedures for immobilizing an immobilizable reaction complex with a negatively charged polymer, described in U.S. application No. 150,278, corresponding to EP Publication No. 0326100, and U.S. application No. 375,029 (EP Publication No. 0406473), can be employed according to the present disclosure to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in U.S. application No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis(succinimidyl) suberate, SPPD 9 succinimidyl 3-[2-pyridyldithio]propionate), SMCC (succinimidyl-4-[Nmaleimidomethyl]cyclohexane-1-carboxylate), SIAB (succinimidyl [4iodoacetyl]aminobenzoate), and SMPB (succinimidyl 4-[1maleimidophenyl]butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. application No. 150,278, filed Jan. 29, 1988, and U.S. application No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

Antibodies

Antibodies useful in the immunoassay methods of the disclosure include polyclonal and monoclonal antibodies. Such polyclonal and monoclonal antibodies can be prepared by any means known in the art. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). It is also possible to isolate antibodies against cell surface antigens by selecting directly on intact cells. The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Labeling Systems

Detectable labels suitable for use in the detection agents of the present disclosure include any composition detectable by spectroscopic, photochemical, biochemical, immunochemical, electrical, optical, or chemical means. Useful labels in the present disclosure include magnetic beads (e.g., Dynabeads™), fluorescent dyes (e.g., fluorescein, Texas Red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3$H, $^{125}$I, $^{35}$S, $^{14}$C, or $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to the detection antibody, as well as to the species-specific antibody, labeling both and providing a composite signal attributable to analyte and autoantibody present in the sample.

Some labels useful according to the disclosure may require the use of an indicator reagent to produce a detectable signal. In an ELISA, for example, an enzyme label (e.g., beta-galactosidase) will require the addition of a substrate (e.g., X-gal) to produce a detectable signal.

Exemplary Formats
Chemiluminescent Microparticle Immunoassay (CMIA)

In an exemplary embodiment a chemiluminescent label is employed in a chemiluminescent microparticle assay (CMIA) according to the disclosure. Generally, chemiluminescent microparticle assay techniques are based on the principle that a chemiluminescent label, when treated via a trigger reagent, will emit light at a characteristic wavelength (i.e., chemiluminescence).

The reactants necessary for CMIA can include microparticles coated with a capture agent specific for the analyte being measured, a chemiluminescent detection agent and a triggering agent (e.g., chemical or electrochemical). The reaction sequence for performing CMIA can include mixing the microparticles coated with a capture agent specific for the analyte with a sample in a reaction vessel to form an immune complex; washing the captured immune complex to remove unbound material; mixing the captured immune complex with a chemiluminescent detection agent; washing the captured immune complex-chemiluminescent detection agent; and mixing the captured immune complex-chemiluminescent detection agent with a triggering agent to initiate light emission.

Chemiluminophores useful in CMIA include acridinium (e.g. acridinium-9-carboxamide), luminol, dioxetane, ruthenium complexes and similar chemiluminescent derivatives. Microparticles useful in CMIA include diamagnetic, magnetic and paramagnetic microparticles. Examples of commercially available automated instruments with which chemiluminescent microparticle assay assays can be conducted include: Architect i-Systems and the Abbott Prism (all available from Abbott Laboratories, Abbott Park, Ill.).

Electrochemical Detection Systems

In other embodiments, immunoassays according to the disclosure are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 µL to 360 µL have been reported previously. In capillary immunoassays with electrochemical detection, the lowest detection limit reported thus far is 3000 molecules of mouse IgG using a volume of 70 µL and a 30 min or 25 min assay time.

In an exemplary embodiment employing electrochemical detection, a capture agent according to the disclosure can be immobilized on the surface of an electrode (the "solid phase"). The electrode is then contacted with a biological sample from, e.g., a human. Analyte in the sample binds to the capture agent to form a solid phase-affixed complex. Anti-analyte antibody, which is labeled with AP, for example, binds to analyte in the complex, thereby becoming immobilized on the surface of the electrode. Any human anti-analyte antibodies present in the sample also bind to analyte in the complex. Anti-human antibody, which is also labeled with AP, binds to any human autoantibodies present, and thereby also becoming immobilized on the surface of the electrode. The addition of PAPP, results in its conversion by AP to $PAP_R$, which is then detected.

Various electrochemical detection systems are described in U.S. Pat. Nos. 7,045,364 (issued May 16, 2006; incorporated herein by reference), 7,045,310 (issued May 16, 2006; incorporated herein by reference), 6,887,714 (issued May 3, 2005; incorporated herein by reference), 6,682,648 (issued Jan. 27, 2004; incorporated herein by reference); 6,670,115 (issued Dec. 30, 2003; incorporated herein by reference).

The present disclosure is for example applicable to point of care assay systems, including Abbott Laboratories' commercial Point of Care (i-STAT™) electrochemical immunoassay system which performs sandwich immunoassays for several cardiac markers, including TnI, CKMB and BNP. Immunosensors and methods of manufacturing and operating them in single-use test devices are described, for example, in U.S. Pat. No. 5,063,081 and published US Patent Application Nos. US 20030170881, US 20040018577, US 20050054078, and US 20060160164, each of which is incorporated herein by reference for their teachings regarding same.

Additionally, it goes without saying that any of the exemplary formats herein, and any assay or kit according to the disclosure can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Multiplex Formats

In particular embodiments, useful, for example, for simultaneously assaying multiple analytes in one biological sample, the solid phase can include a plurality different capture agents. Thus, for example, the solid phase can have affixed thereon a plurality of anti-analyte capture antibodies, wherein each antibody is specific for a different analyte. In an exemplary embodiment, the solid phase can consist of a plurality of different regions on a surface, wherein each region has affixed antibodies of a particular specificity.

Multiplex formats can, but need not, employ a plurality of labels, wherein each label is used for the detection of a particular analyte and/or auto-antibodies specific for that analyte. For example, multiple analytes can be detected without using a plurality of labels where a plurality of capture agents, such as anti-analyte capture antibodies, are affixed to the solid phase at different known locations, based on specificity. Because the specificity of the capture agent at each location is known, the detection of a signal at a particular location can be associated with the presence of analyte and/or anti-analyte autoantibodies bound at that location. Examples of this format include microfluidic devices and capillary arrays, containing different capture agents at different locations along a channel or capillary, respectively, and microarrays, which typically contain different capture agents arranged in a matrix of spots ("target elements") on a surface of a solid support. In particular embodiments, each different capture agent can be affixed to a different electrode, which can, for example, be formed on a surface of a solid support, in a channel of a microfluidic device, or in a capillary.

Test Kits

The disclosure also provides test kits. Test kits according to the disclosure include one or more reagents useful for practicing one or more immunoassays according to the disclosure. A test kit generally includes a package with one or more containers holding the reagents, as one or more separate compositions or, optionally, as admixture where the compatibility of the reagents will allow. The test kit can also include other material(s) that may be desirable from a user standpoint, such as a buffer(s), a diluent(s), a standard(s), and/or any other material useful in sample processing, washing, or conducting any other step of the assay.

In one embodiment, a test kit includes: (a) a labeled detection agent specific for an analyte; and (b) a labeled species-specific antibody, wherein the labeled species-specific antibody is specific for the species from which the biological sample was obtained. In particular embodiments, the labeled detection agent includes a labeled anti-analyte antibody. The labeled anti-analyte antibody can be labeled with the same label as the labeled species-specific antibody or can be labeled with a different label. The labeled anti-analyte antibody and the labeled species-specific antibody can be packaged in the same container or in different containers. In preferred embodiments, the species-specific antibody is a human-specific antibody.

In particular embodiments, the test kit includes at least one direct label, such as acridinium-9-carboxamide. Test kits according to the disclosure can also include at least one indirect label. If the label employed generally requires an indicator reagent to produce a detectable signal, the test kit preferably includes one or more suitable indicator reagents.

Test kits according to the disclosure can additionally include a solid phase and a capture agent, such as an anti-analyte capture antibody, affixed to the solid phase. In exemplary embodiments, the solid phase includes one or more microparticles (e.g., magnetic or paramagnetic microparticles), electrodes, and/or a microplate. Test kits designed for multiplex assays conveniently contain one or more solid phases including a plurality of anti-analyte capture antibodies that are specific for a plurality of different analytes. Thus, for example, a test kit designed for multiplex electrochemical immunoassays can contain a solid phase including a plurality of electrodes, with each electrode bearing a different anti-analyte capture antibody. Alternatively, a test kit intended for multiplex "sandwich" immunoassays can include a plurality of different labeled anti-analyte antibodies that are specific for the plurality of different analytes, wherein each different labeled anti-analyte antibody is labeled with a distinct label.

Test kits according to the disclosure preferably include instructions for carrying out one or more of the immunoassays of the disclosure. Instructions included in kits of the disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Adaptation of Kit and Method

The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the detection agent or capture agent (e.g., an anti-analyte, monoclonal or polyclonal antibody) is attached, and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format, such as an ELISA, may incubate a detection antibody, such as the conjugate reagent, for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an analyte assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized anti-analyte, monoclonal and/or polyclonal antibody (or a fragment thereof, a variant thereof, or a fragment of a variant thereof) are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising a specific binding partner for an analyte, such as an anti-analyte, monoclonal/polyclonal antibody (or a fragment thereof, a variant thereof, or a fragment of a variant thereof that can bind the analyte), which can be detectably labeled. Within the fluid pouch of the cartridge is an aqueous reagent that includes p-aminophenol phosphate.

In operation, a sample suspected of containing an analyte is added to the holding chamber of the test cartridge, and the cartridge is inserted into the I-STAT® reader. After the specific binding partner (e.g., antibody) for an analyte has dissolved into the sample, a pump element within the cartridge forces the sample into a conduit containing the chip. Here it is oscillated to promote formation of the sandwich. In the penultimate step of the assay, fluid is forced out of the pouch and into the conduit to wash the sample off the chip and into a waste chamber. In the final step of the assay, a label such as an alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, microparticle diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-Stat cartridge format, using a nucleic acid sequence linked to the signal antibody as a signal amplifier.

The disclosure will be better understood through examples illustrating its use and efficacy. The following example is offered to illustrate, but not to limit, the claimed invention.

EXAMPLE

Effect of Anti-Human Conjugate Addition on Cardiac Troponin-I Detection with/without Anti-Cardiac Troponin Autoantibody Two samples were chosen from a population of normal blood donors screened for anti-cardiac troponin-I autoantibodies using a cTnI-coated microplate and reagents from the ARCHITECT® STAT-Troponin I kit (Abbott Laboratories, Abbott Park, Ill., catalog number 2K41-30) as described in U.S. patent application Ser. No. 11/588,073 (published as US Patent Application 20080102481 and incorporated herein in its entirety for its teachings regarding same). One sample was determined to have low-reactivity (LR) in the assay while the other had high reactivity (HR). Cardiac troponin-I (BiosPacific, Emeryville, Calif., catalog number J34170359) was added to aliquots of each sample at two concentrations to give final cTnI concentrations of 0.25 and 1.5 ng/mL. Each sample was analyzed using the ARCHITECT® STAT-Troponin-I kit on an ARCHITECT® i2000SR instrument (Abbott Laboratories, Abbott Park, Ill.) with an addition of an anti-human IgG acridinium-9-carboxamide conjugate (25 ng/mL) (as described in U.S. patent application Ser. No. 11/588,073, published as US Patent Application 20080102481) to the mouse anti-troponin acridinium-9-carboxamide chemiluminescent detection conjugate normally supplied with the kit.

Figure 1A:
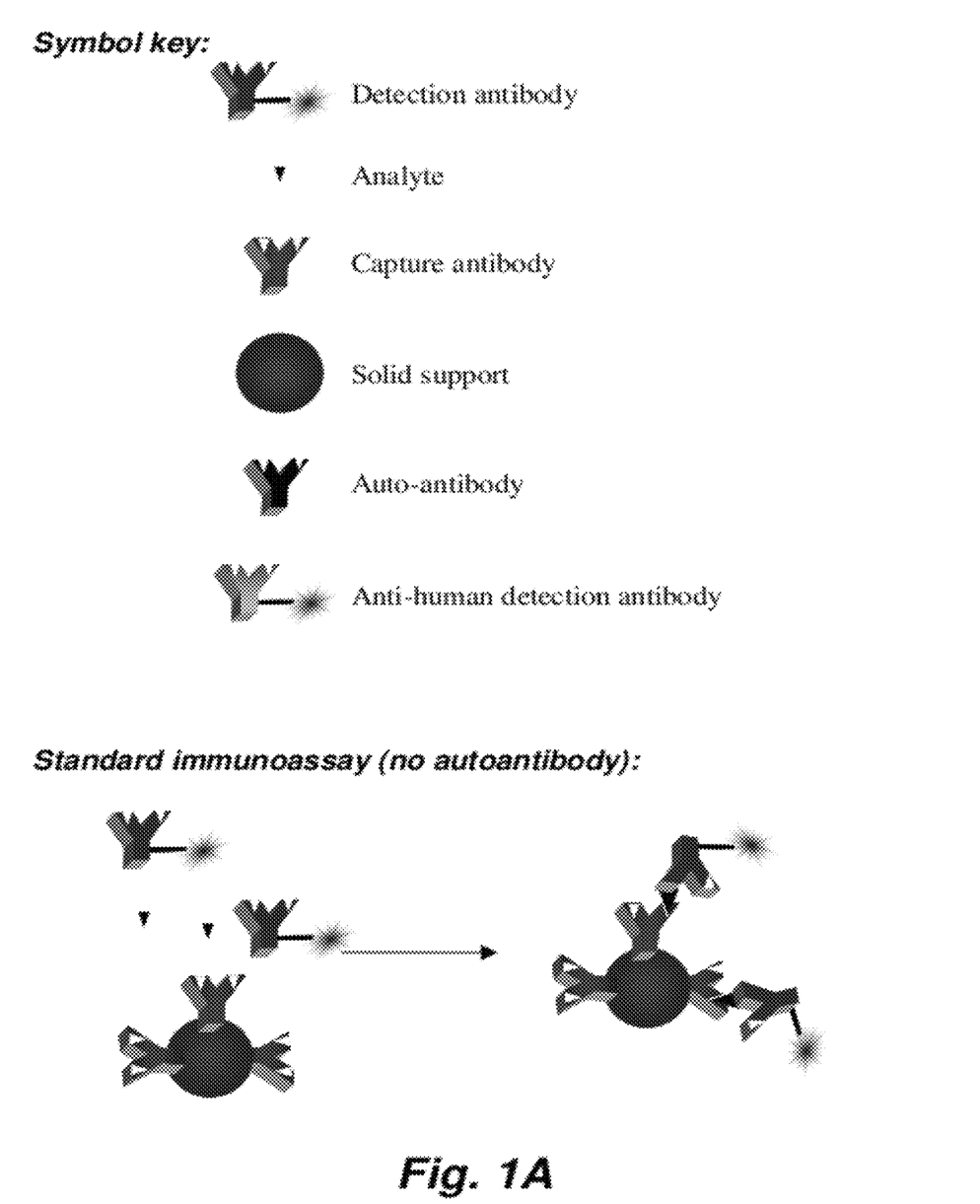
FIG. 1A (including the Symbol key) shows the typical assay configuration, where, in the absence of interfering endogenous antibodies (e.g., autoantibodies), signal from a labeled anti-analyte antibody is proportional to the concentration of analyte in the sample.
Figure 1B:
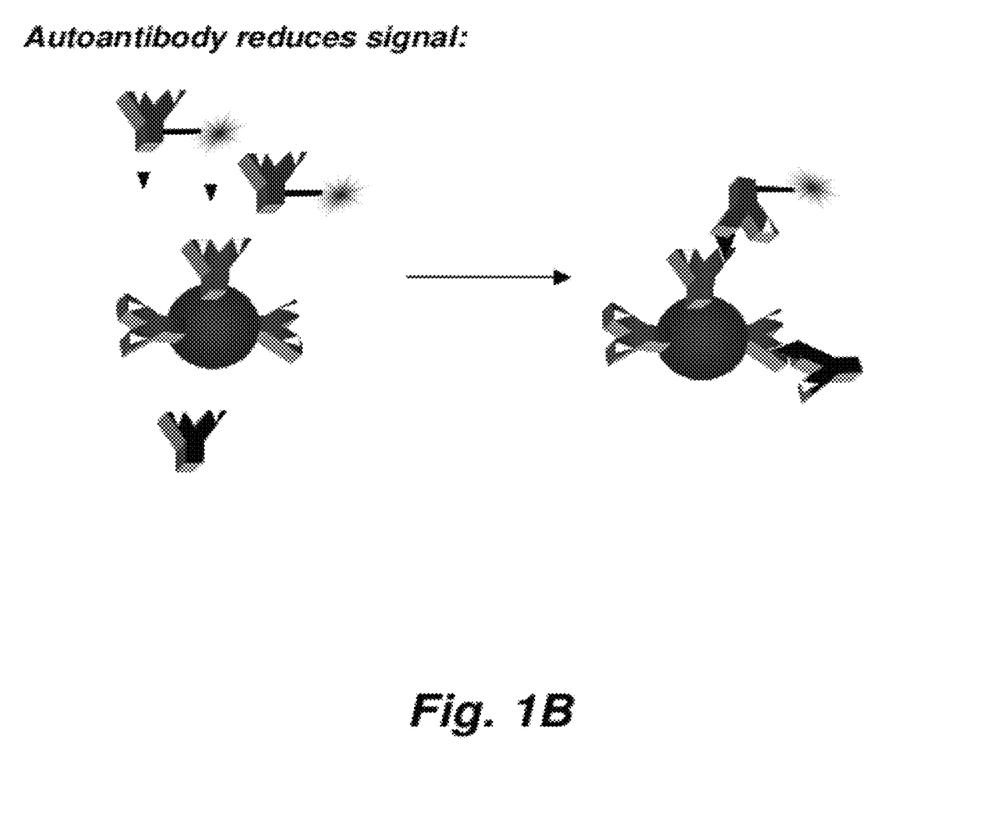
FIG. 1B (employing the same Symbols) shows that in the presence of interfering endogenous antibodies (e.g., autoantibodies), the signal from the labeled anti-analyte antibody is diminished.
Figure 2:
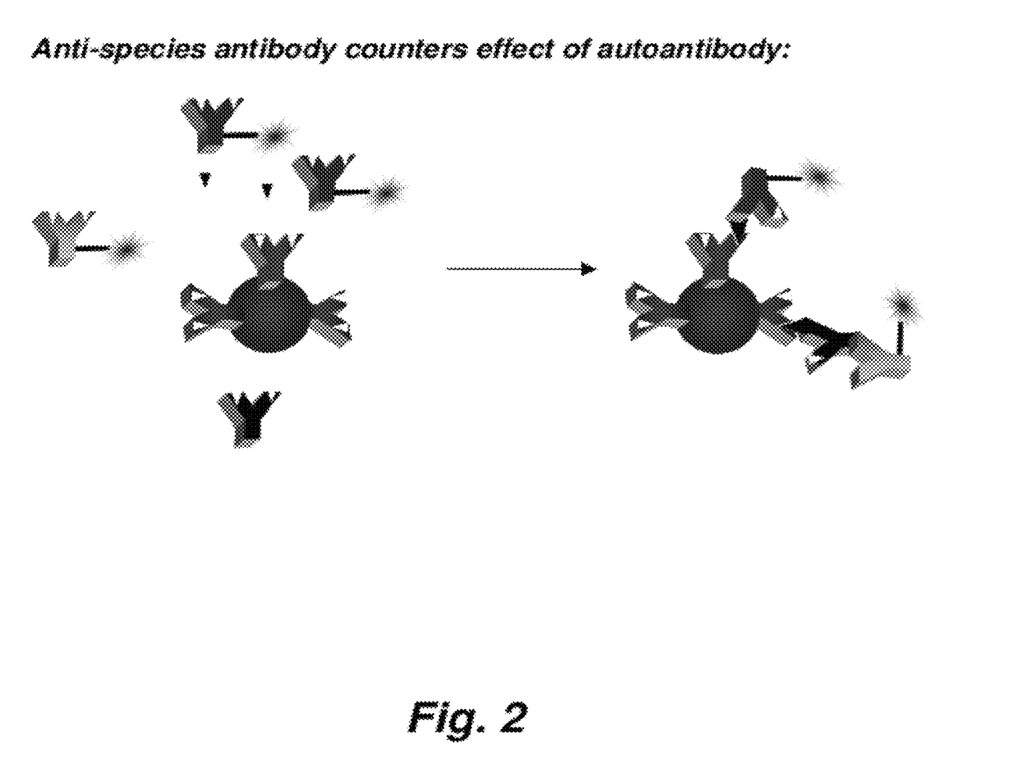
Figure 3:
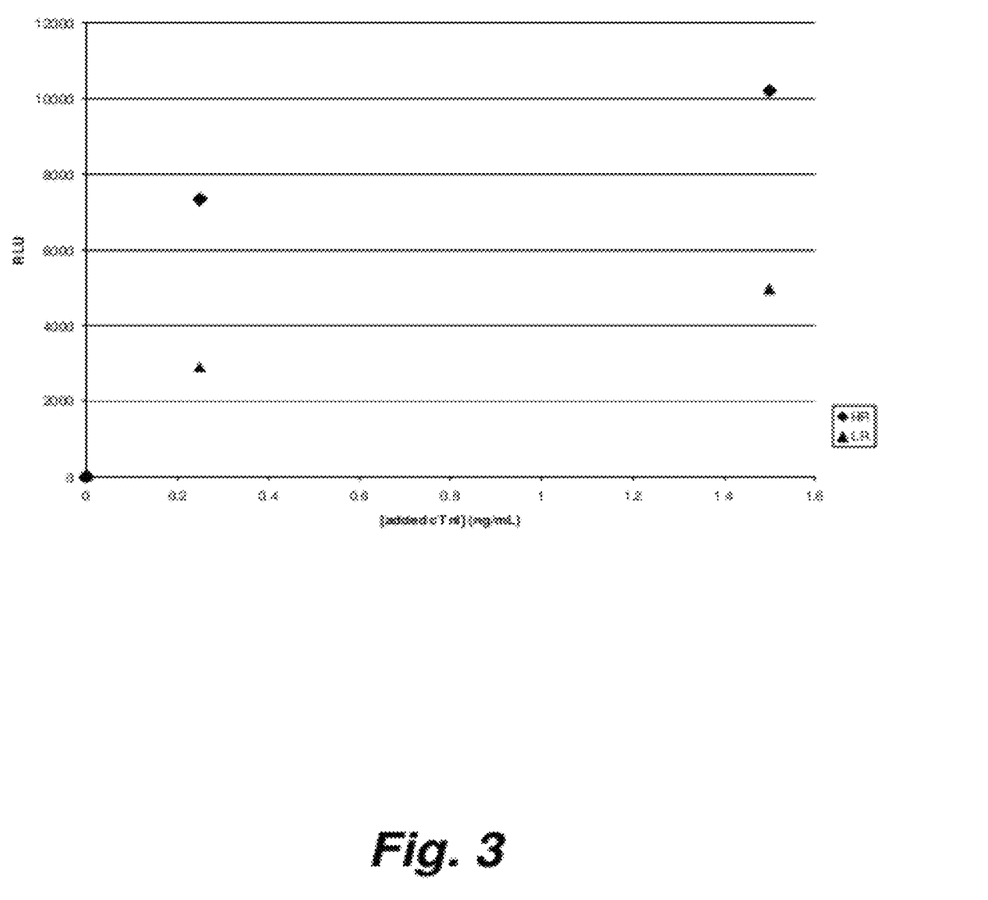
FIG. 3 is a graph showing cardiac troponin I (cTnI) concentration effect on chemiluminescent signal (reported in Relative Light Units, or "RLUs") as described in the Example. Symbols: solid diamonds, high reactivity sample (HR); solid triangles, low reactivity sample (LR).

FIG. 3 shows that the addition of a chemiluminescent anti-human IgG conjugate increases the dose-response to troponin in samples containing cardiac troponin-I autoantibodies. The magnitude of the improvement is at least two-fold.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention. All patents and publications mentioned in the specification are indicative of the levels of those skilled in the art to which the invention pertains.

U.S. patent application Ser. No. 11/588,073 published as US Patent Application 20080102481 describes among other things assays for cardiac troponin autoantibodies and is incorporated herein by reference in its entirety for its teachings regarding same.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An immunoassay method for an analyte of interest in a biological sample that may contain endogenous anti-analyte antibodies, said method comprising:
    (a) contacting a biological sample being tested for analyte with a capture agent affixed to a solid phase, wherein the capture agent binds analyte, under conditions sufficient for binding of the capture agent to analyte to form a solid phase-affixed capture agent/analyte complex, and:
        (i) a detection agent that binds the analyte, under conditions sufficient for binding of the detection agent to any analyte present in the capture agent/analyte complex so as to form a solid phase-affixed detection agent/analyte/capture agent complex; and
        (ii) a species-specific antibody, wherein the species-specific antibody is specific for the species from which the biological sample was obtained and specifically binds endogenous anti-analyte antibody, under conditions sufficient for specific binding of the species-specific antibody to any endogenous anti-analyte antibody present in the sample and bound to the capture agent/analyte complex so as to form a solid phase-affixed species-specific antibody/endogenous anti-analyte antibody/analyte/capture agent complex; and
    (b) detecting analyte by detecting a signal from the solid phase-affixed complex(es) set forth in (a),
    wherein the signal is positively correlated with the concentration of analyte present in the sample.

2. The immunoassay method of claim 1, wherein the detection agent and the capture agent bind to different sites on the analyte.

3. The immunoassay method of claim 1, wherein the detection agent and the species-specific antibody are labeled with the same label.

4. The immunoassay method of claim 1, wherein the biological sample is contacted with the detection agent and the species-specific antibody simultaneously.

5. The immunoassay method of claim 1, wherein the biological sample is contacted with the detection agent and the species-specific antibody sequentially.

6. The immunoassay method of claim 1, wherein the contacting of (a)(i) and/or (a)(ii) is carried out simultaneously with the contacting of the biological sample with the capture agent.

7. The immunoassay method of claim 1, wherein the contacting (a)(i) and/or (a)(ii) is carried out sequentially with the contacting of the biological sample with the capture agent.

8. An immunoassay method for an analyte of interest in a biological sample that may contain anti-analyte autoantibodies, said method comprising:
    (a) contacting a biological sample being tested for the analyte with a capture agent affixed to a solid phase wherein the capture agent binds analyte, under conditions sufficient for binding of the capture agent to analyte to form a solid phase-affixed capture agent/analyte complex;
    (b) contacting the biological sample with:
        (i) a detection agent that binds the analyte under conditions sufficient for binding of the detection agent to any analyte present in the capture agent/analyte complex so as to form a solid phase-affixed detection agent/analyte/capture agent complex; and
        (ii) a species-specific antibody, wherein the species-specific antibody is specific for the species from which the biological sample was obtained and specifically binds anti-analyte autoantibody, under conditions sufficient for specific binding of the species-specific antibody to any anti-analyte autoantibody bound to the capture agent/analyte complex so as to form a solid phase-affixed species-specific antibody/anti-analyte autoantibody/analyte/capture agent complex; and
    (c) detecting analyte by detecting a signal from the solid phase-affixed complex(es) set forth in (b),
    wherein the signal is positively correlated with the concentration of analyte present in the sample.

9. An immunoassay method for an analyte of interest in a biological sample that may contain anti-analyte autoantibodies, said method comprising:
    (a) contacting a biological sample being tested for the analyte with an anti-analyte capture antibody affixed to a solid phase wherein the capture antibody specifically binds analyte, under conditions sufficient for specific binding of the capture antibody to analyte to form a solid phase-affixed capture antibody/analyte complex;
    (b) contacting the biological sample with:
        (i) an anti-analyte antibody that binds the analyte under conditions sufficient for specific binding of the anti-analyte antibody to any analyte present in the capture antibody/analyte complex so as to form a solid phase-affixed anti-analyte antibody/analyte/capture antibody complex; and
        (ii) a species-specific antibody, wherein the species-specific antibody is specific for the species from which the biological sample was obtained and specifically binds anti-analyte autoantibody, under conditions sufficient for specific binding of the species-specific antibody to any anti-analyte autoantibody bound to the capture antibody/analyte complex so as to form a solid phase-affixed species-specific antibody/anti-analyte autoantibody/analyte/capture antibody complex; and
    (c) detecting analyte by detecting a signal from the solid phase-affixed complex(es) set forth in (b),
    wherein the signal is positively correlated with the concentration of analyte present in the sample.

10. The immunoassay method of claim 9, wherein the anti-analyte antibody and the species-specific antibody are labeled with the same label.

11. The immunoassay method of claim 9, wherein the contacting of (a) and the contacting of (b)(i) and/or (b)(ii) is carried out simultaneously.

12. The immunoassay method of claim 9, wherein the contacting of (a) and the contacting of (b)(i) and/or (b)(ii) is carried out sequentially.

13. The immunoassay method of claim 9, wherein the biological sample is contacted with the anti-analyte antibody and the species-specific antibody simultaneously.

14. The immunoassay method of claim 9, wherein the biological sample is contacted with the anti-analyte antibody and the species-specific antibody sequentially.

15. The immunoassay method of claim 9, wherein the biological sample is obtained from a human.

16. The immunoassay method of claim 9, wherein at least one label comprises a direct label.

17. The immunoassay method of claim 16, wherein the direct label comprises an acridinium-9-carboxamide.

18. The immunoassay method of claim 9, wherein at least one label comprises an indirect label.

19. The immunoassay method of claim 9, wherein the detecting of (c) comprises contacting at least one label with an indicator reagent.

20. The immunoassay method of claim 9, wherein the solid phase comprises a microparticle.

21. The immunoassay method of claim 20, wherein the microparticle is magnetic or paramagnetic.

22. The immunoassay method of claim 9, wherein the solid phase comprises a microplate.

23. The immunoassay method of claim 9, wherein the solid phase comprises an electrode.

24. The immunoassay method of claim 9, wherein the solid phase comprises a plurality of anti-analyte capture antibodies that are specific for a plurality of different analytes.

25. The immunoassay method of claim 24, wherein the biological sample is contacted with a plurality of different anti-analyte antibodies that are specific for said plurality of different analytes, wherein each different anti-analyte antibody is labeled with a distinct label.

26. The immunoassay method of claim 24, wherein the solid phase comprises a plurality of electrodes, each electrode bearing a different anti-analyte capture antibody.

* * * * *